United States Patent
Vettoretti et al.

(10) Patent No.: US 11,749,408 B2
(45) Date of Patent: Sep. 5, 2023

(54) INDIVIDUALIZED MULTIPLE-DAY SIMULATION MODEL OF TYPE 1 DIABETIC PATIENT DECISION-MAKING FOR DEVELOPING, TESTING AND OPTIMIZING INSULIN THERAPIES DRIVEN BY GLUCOSE SENSORS

(71) Applicant: DexCom, Inc., San Diego, CA (US)

(72) Inventors: Martina Vettoretti, Valla di Riesse P (IT); Andrea Facchinetti, Trissino (IT); Giovanni Sparacino, Padua (IT); Claudio Cobelli, Padua (IT)

(73) Assignee: DEXCOM, INC., San Diego, CA (US)

( * ) Notice: Subject to any disclaimer, the term of this patent is extended or adjusted under 35 U.S.C. 154(b) by 0 days.

(21) Appl. No.: 17/451,609

(22) Filed: Oct. 20, 2021

(65) Prior Publication Data
US 2022/0044813 A1 Feb. 10, 2022

Related U.S. Application Data

(62) Division of application No. 15/158,047, filed on May 18, 2016, now Pat. No. 11,183,301.
(Continued)

(51) Int. Cl.
*G08B 21/04* (2006.01)
*G16H 50/20* (2018.01)
(Continued)

(52) U.S. Cl.
CPC .......... *G16H 50/20* (2018.01); *A61M 5/1723* (2013.01); *G16H 20/17* (2018.01); *G16H 40/60* (2018.01);
(Continued)

(58) Field of Classification Search
USPC ...... 340/539.12, 539.22, 539.32, 568.1, 683, 340/691.2, 686.6, 691.6, 693.8
See application file for complete search history.

(56) References Cited

U.S. PATENT DOCUMENTS 8,548,544 B2 10/2013 Kircher et al.
8,707,392 B2 4/2014 Birtwhistle et al.
(Continued)

FOREIGN PATENT DOCUMENTS

WO WO-2007149533 A2 12/2007
WO WO-2008101172 A2 8/2008
WO WO-2012178134 A2 12/2012

OTHER PUBLICATIONS

Ambrosiadou B.V., et al., "Clinical Evaluation of Diabetes Expert System for Decision Support by Multiple Regimen Insulin Dose Adjustment," Computer Methods & Programs in Biomedicine, vol. 49, 1996, pp. 105-115.
(Continued)

*Primary Examiner* — Daniel Previl
(74) *Attorney, Agent, or Firm* — FIG. 1 Patents

(57) ABSTRACT

A mathematical model of type 1 diabetes (T1D) patient decision-making can be used to simulate, in silico, realistic glucose/insulin dynamics, for several days, in a variety of subjects who take therapeutic actions (e.g. insulin dosing) driven by either self-monitoring blood glucose (SMBG) or continuous glucose monitoring (CGM). The decision-making (DM) model can simulate real-life situations and everyday patient behaviors. Accurate submodels of SMBG and CGM measurement errors are incorporated in the comprehensive DM model. The DM model accounts for common errors the patients are used to doing in their diabetes management, such as miscalculations of meal carbohydrate content, early/delayed insulin administrations and missed insulin boluses. The DM model can be used to assess in
(Continued)

silico if/when CGM can safely substitute SMBG in T1D management, to develop and test guidelines for CGM driven insulin dosing, to optimize and individualize off-line insulin therapies and to develop and test decision support systems.

20 Claims, 7 Drawing Sheets

Related U.S. Application Data

(60) Provisional application No. 62/163,091, filed on May 18, 2015.

(51) Int. Cl.
| | | |
|---|---|---|
| G16H 50/50 | (2018.01) | |
| G16H 20/17 | (2018.01) | |
| G16H 40/60 | (2018.01) | |
| A61M 5/172 | (2006.01) | |

(52) U.S. Cl.
CPC ......... *G16H 50/50* (2018.01); *A61M 2205/50* (2013.01); *A61M 2230/005* (2013.01); *A61M 2230/201* (2013.01)

(56) References Cited

U.S. PATENT DOCUMENTS

| | | | |
|---|---|---|---|
| 8,954,373 B2 | 2/2015 | Atlas et al. | |
| 9,827,372 B2 | 11/2017 | Dobbles et al. | |
| 10,561,351 B2* | 2/2020 | Lucisano | A61B 5/0031 |
| 2006/0272652 A1 | 12/2006 | Stocker et al. | |
| 2007/0055799 A1* | 3/2007 | Koehler | G16H 40/63 710/62 |
| 2007/0083335 A1* | 4/2007 | Moerman | G01N 21/8483 702/19 |
| 2008/0220403 A1 | 9/2008 | Marling et al. | |
| 2009/0006129 A1 | 1/2009 | Thukral et al. | |
| 2009/0164190 A1 | 6/2009 | Hayter | |
| 2009/0164251 A1* | 6/2009 | Hayter | G16H 20/10 705/3 |
| 2010/0179768 A1 | 7/2010 | Kovatchev et al. | |
| 2010/0280441 A1 | 11/2010 | Wilinska et al. | |
| 2010/0292634 A1 | 11/2010 | Kircher, Jr. et al. | |
| 2011/0098548 A1 | 4/2011 | Budiman et al. | |
| 2011/0106011 A1 | 5/2011 | Cinar et al. | |
| 2011/0178499 A1 | 7/2011 | Brukalo et al. | |
| 2014/0031786 A1 | 1/2014 | Kircher, Jr. et al. | |
| 2014/0052095 A1 | 2/2014 | Dobbles et al. | |
| 2014/0060145 A1* | 3/2014 | Hoss | G01D 18/00 73/1.03 |
| 2015/0134356 A1 | 5/2015 | Atlas et al. | |
| 2016/0004813 A1* | 1/2016 | Kovatchev | G16B 5/00 702/19 |
| 2016/0342754 A1 | 11/2016 | Vettoretti et al. | |

OTHER PUBLICATIONS

Bailey T.S et al., "Clinical Accuracy of a Continuous Glucose Monitoring System with an Advanced Algorithm," J Diabetes Science & Technology, 2015, vol. 9 (2), pp. 209-214.
Benharref A., et al., "Closing this Loop from Continuous M-health Monitoring to Fuzzy Logic-based Optimized Recommendations," Conference on the Proceedings IEEE Eng. Med. Biol. Soc. 2014, pp. 2698-1701.
Bergman R.N., et al., "Physiologic Evaluation of factors Controlling Glucose tolerance in man: Measurement of insulin sensitivity and beta-cell glucose sensitivity from the the response to intravenous glucose," J Clin Invest. Dec. 1981, vol. 68 (6), pp. 1456-1467.
Burdick J., et al., "Missed Insulin Meal Boluses and Elevated Haemoglobin A1c levels in Children Receiving Insulin Pump Therapy Pediatrics," 2004, vol. 113 (3),pp. E221-E224.

Carrier J.M., et al., "Modeling the Adoption Patterns of New Health Care Technology with Respect to Continuous Glucose Monitoring Systems and Information Engineering Designs," Apr. 25, 2008, pp. 249-254.
Chiara D.M., et al., "The UVA/PADOVA type I Diabetes Simulator: New Features," J Diab Sci. and Tech, vol. 8(1), pp. 26-34.
Colmegna P., et al., "Analysis of Three TIDM Simulating Models for Evaluating Robust Closed-Loop Controllers," Computer Methods and Programs in Biomed, vol. 113 (1), 2004, pp. 371-382.
Davidson P.C., et al., "Analysis of Guidelines for Basal-Bolus Insulin Dosing: Basal Insulin, Correction Factor and Carbohydrate to Insulin Ratio," Endocr Pract, 2008, vol. 14 (9), pp. 1095-1110.
European Office Action for Application No. 16730077.1 dated May 4, 2020.
Facchinetti A., et al., "Modeling the Glucose Sensor Error," IEEE Trans Biomed Eng BME, vol. 61 (3), Mar. 2014, pp. 620-629.
Garg S., et al. "Improvement in Glycemic Excursions with a Transcutaneous, Real-Time Continuous Glucose Sensor: A Randomized Controlled Trial," Diabetes Care, vol. 29(1), 2006, pp. 44-50.
Glorennec et al., "Predictive Fuzzy Model of Glycaemic Variations," Fuzzy Logic and Soft Computing, 1995, pp. 411-420.
Hoss U., et al.."Continuous glucose monitoring in the subcutaneous tissue over a 14-day sensor wear period," J Diabetes Science & Technology, Sep. 2013, vol. 7 (5), pp. 1210-1219.
International Preliminary Report on Patentability for Application No. PCT/US2016/033106 dated Nov. 30, 2017, 13 pages.
International Search Report and Written opinion for Application No. PCT/US2016/033106 dated Oct. 24, 2016, 16 pages.
JDRF CGM Study Group, "JDRF Randomized Clinical Trial to Assess the Efficacy of Real Time Continuous Glucose Monitoring in the Management of Type 1 diabetes: Research Design and Methods," vol. 10 (4), 2008, 15 pages.
Karon B.S., et al., "Empiric Validation of Simulation Models for Estimating Glucose Meter Performance Criteria for Moderate Levels of Glycemic Control," Diabetes Technology and Therapeutics, Dec. 2013, vol. 15 (12), pp. 996-1003.
Kovatchev P.B., et al., "Assessing Sensor Accuracy for Non-Adjunct Use of Continuous Glucose Monitoring," Diabetes Technology & Therapeutics, 2015, vol. 17 (3), pp. 177-186.
Lane E.J., et al., "Continuous Glucose Monitors: Current Status and Future Developments," Current Opinion endocrine, Diabetes and Obesity, Apr. 2013, vol. 20 (2), 9 pages.
Merriam-Webster Online dictionary, Definition of "Estimate" available at https://www.merriam-webster.com/dictionary/estimate, accessed Dec. 5, 2020, 16 pages.
Pettus J., et al., "How Patients with Type 1 Diabetes Translate Continuous Glucose Monitoring Data into Diabetes Management Decisions," Endocrinol Pract., vol. 21 (6), 2015, pp. 613-620.
Schwartz F.L., et al., "Evaluating the Automated Blood Glucose Pattern Detection and Case-Retrieval Modules of the 4 Diabetes Support System", J Diabetes Science & Technology, vol. 4(6), 2010, pp. 1563-1569.
Stadelmann A., et al., "DIABETEX Decision Module 2: Calculation of Insulin dose Proposals and Situation Recognition by means of Classifiers," Computer Methods Programs in Biomed, 1990, vol. 32, pp. 333-337.
"Use of the DirectNet Applied Treatment Algorithm (DATA) for Diabetes Management with Real-time Continuous," Diabetes Research in Children Network (DirectNet) Study Group, Apr. 2008, vol. 9(2), pp. 142-147.
Vettoretti M. et al., "A model of self-monitoring blood glucose measurement error", J Diabetes Sci Technol. 2017, 11(4):724-735; Epub Mar. 16, 2017, 1-12.
Vettoretti M. et al., "A Stochastic Model of Self-monitoring of Blood Glucose Measurement Error: Toward a Simulator of Diabetic Patient Therapeutic Decisions", (Abstract 381) Advanced Technologies & Treatment for Diabetes Conference, Paris, France—Feb. 18-21, 2015, p. A-165.
Visentin R., et al., "Circadian Variability of Insulin Sensitivity: Physiological input for in Silica artificial Pancreas," Diabetes Technology & Therapeutics, 2015, vol. 17(1), pp. 1-7.

(56) References Cited

OTHER PUBLICATIONS

Zahlmann et al., "DIABETEX—A Decision Support System for Therapy of Type 1 Diabetic Patients", Computer methods & programs in biomedicine, 1990, vol. 32, pp. 297-301.

* cited by examiner

INDIVIDUALIZED MULTIPLE-DAY SIMULATION MODEL OF TYPE 1 DIABETIC PATIENT DECISION-MAKING FOR DEVELOPING, TESTING AND OPTIMIZING INSULIN THERAPIES DRIVEN BY GLUCOSE SENSORS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a division of U.S. application Ser. No. 15/158,047, filed May 18, 2016, which claims the benefit of U.S. Provisional Application No. 62/163,091, filed May 18, 2015, the disclosure of which is hereby expressly incorporated by reference in its entirety and is hereby expressly made a portion of this application.

FIELD OF THE INVENTION

An individualized multiple-day comprehensive simulation model of Type 1 Diabetes (T1D) patient decision-making for therapeutic actions such as insulin dosing driven by either Self-Monitored Blood Glucose (SMBG) or Continuous Glucose Monitoring (CGM) measurements is provided. The simulation model can be used to compare and optimize in silico SMBG versus CGM driven insulin therapies for T1D patients, to test candidate guidelines for CGM-driven insulin dosing, to optimize and individualize off-line insulin therapies and to develop and test decision support systems.

BACKGROUND OF THE INVENTION

The Conventional Management of Type 1 Diabetes

In healthy individuals, blood glucose (BG) concentration is finely maintained within the normal range, 70-180 mg/dl, by insulin, a hormone produced by the pancreatic beta-cells. In T1D, the absence of insulin secretion leads BG concentration out of control. While hyperglycemia (BG>180 mg/dl) can produce long-term complications (e.g. cardiovascular disease, neuropathy, nephropathy and retinopathy), hypoglycemia (BG<70 mg/dl) is dangerous in the short-term (e.g. seizure, coma and death). Conventional T1D therapy is based on insulin administrations, done by the patient himself by multiple daily injections (MDI) or continuous subcutaneous insulin infusion (CSII), according to a basal-bolus insulin regimen in which insulin boluses are injected at mealtime to cover food intake (or, if necessary, after a meal to correct a post-prandial hyperglycemia), while basal insulin is administered to maintain a normal glucose level in absence of meal perturbation, typically during the night. Pre-meal insulin boluses are calculated in two steps: firstly, the insulin dose required to cover the meal is determined on the basis of estimated meal carbohydrate content; then, the obtained meal bolus is corrected according to the current BG concentration. In particular, at present time, portable finger stick devices for self-monitoring of blood glucose (SMBG) are the only BG monitoring systems approved by the U.S. Food and Drug Administration (FDA) for insulin dosing. However, given the relative invasiveness and patient discomfort, SMBG devices usually collect only a few measurements per day (usually 3-4). Given the sparseness of sampling, SMBG-driven therapy is clearly far from being optimal in order to prevent dangerous hyper/hypoglycemic events that could happen, e.g., after a meal or during nighttime.

Use of Continuous Glucose Monitoring Sensors in T1D Management

Continuous glucose monitoring (CGM) sensors measure, almost continuously (every 1-5 minutes), the interstitial glucose (IG) concentration in the subcutaneous tissue. Several studies have recently demonstrated that CGM is able to detect or even predict hypo/hyperglycemic events, leading remarkable benefits to the quality of glycemic control. Nevertheless, at the level of agencies such as FDA, CGM is actually approved to be an adjunct to SMBG only and not a replacement. In fact, evidence that using CGM for insulin dosing is as safe as using SMBG starts accumulating, but it is still not definitive. The recent significant improvement achieved in accuracy by the last generation CGM devices calls for the design of studies aiming at understanding if CGM sensors can lead to efficient and clinically safe therapeutic decisions.

Simulation of T1D Decision Making: State of the Art

Software to simulate glucose profiles of virtual patients with diabetes was proposed. The system allows selection a specific scenario and a specific virtual patient and run simulations by a glucose-insulin model to calculate the efficacy of certain insulin dosing. However, the system does not include a model of the device used by the patient for glucose monitoring (either a SMBG device or a CGM sensor) which is fundamental to perform realistic in silico tests of T1D insulin therapies. Another limitation of the method is the model used to describe patient glucose-insulin dynamics, which results too simple for an appropriate description of T1D patients' physiology (e.g. does not account for the intra-individual patient variability).

A model-based method to determine insulin therapy requirements on the basis of patient CGM and insulin pump data has been presented. The method employs the extended version of the glucose minimal model to simulate variations in plasma glucose concentration driven by certain variations of plasma insulin. Method's limitations include the pseudo steady-state assumption about patient's blood glucose level and the model linearization performed to estimate patient model parameters. Moreover the method of does not take into account the influence of SMBG/CGM error on insulin dosing.

A simulation study assessing the non-adjunct use of the CGM sensor was recently conducted, where CGM and insulin pump data and a linearized model of glucose-insulin dynamics were used to reproduce in silico BG profiles obtained by different insulin dosing patterns. However, the method suffers from several key limitations: it is based on the use of a suboptimal linearized glucose-insulin model, which is known to be inappropriate to describe patient physiology; it uses population model parameters and thus it does not take into account the large variability among different individuals, as well as the inter- and intra-day patient variability (this does not allow a proper—optimal—insulin tuning); and it works only retrospectively, since it can be used only to re-adjust the therapy on the same day in which data have been acquired, limiting the domain of validity not allowing multiple (future) days of simulation.

A method based on a more complex and complete compartmental model of T1D patient glucose-insulin system which allows a more accurate description of glucose-insulin dynamics in T1D than other models has been proposed and allows running simulations in a wide population of virtual subjects. The model includes an insulin pump submodel and a CGM submodel that allows testing continuous-time monitoring and control strategies in T1D. However, the model does not allow running multi-day simulations since it does not take into account time-variability of insulin sensitivity. Other limitations are the lack of a comprehensive model of T1D therapy and the absence of a model of SMBG measurement error, thus it is not possible to test in silico SMBG-driven insulin therapies.

Remarkably, neither of the previous model-based simulation methods allows testing of T1D insulin therapies based on either SMBG or CGM in a realistic scenario because of the absence of model of real patients decision-making actions taking into account all the possible errors the patients are used to doing in their diabetes management e.g. miscalculation of meal carbohydrate content, early/delayed insulin doses administrations and missed boluses occurrence.

Technical and patent literature relating to measurement of blood glucose, insulin dosing, and other aspects of T1D management include: P. C. Davidson et al., "Analysis of guidelines for basal-bolus insulin-dosing: basal insulin, correction factor and carbohydrate-to-insulin ration", Endocr. Pract., vol. 14, no. 9, pp. 1095-1101, 2008; J. E. Lane et al., "Continuous glucose monitors: current status and future developments", Curr. Opin. Endocrinol. Diabetes Obes., vol. 20, no. 2, pp. 106-111, 2013; S. Garg et al. "Improvement in glycemic excursions with a transcutaneous, real-time continuous glucose sensor: a randomized controlled trial", Diabetes Care, vol. 29, pp. 44-50, 2006; T. S. Bailey, A. Chang, M. Christiansen, "Clinical accuracy of a continuous glucose monitoring system with an advanced algorithm", J. Diabetes Sci. Technol., vol. 9, no. 2, pp. 209-214, 2015; U. Hoss, E. S. Budiman, H. Liu and M. P. Christiansen, "Continuous glucose monitoring in the subcutaneous tissue over a 14-day sensor wear period", J. Diabetes Sci. Technol., vol. 7, no. 5, pp. 1210-1219, 2013; D. N. Stocker, S. Kanderian, G. J. Cortina et al., "Virtual patient software system for educating and treating individuals with diabetes", US Patent Application Publication, no. US2006/0272652A1; E. S. Budiman, N. Crouther, T. Dunn et al., "Methods for modeling insulin therapy requirements", US Patent Application Publication, no. US2011/0098548A1; R. N. Bergman, L. S. Phillips and C. Cobelli, "Physiologic evaluation of factors controlling glucose tolerance in man: measurement of insulin sensitivity and beta-cell glucose sensitivity from the response to intravenous glucose", J Clin Invest, vol. 68, no. 6, pp. 1456-1467, December 1981; B. P. Kovatchev et al., "Assessing sensor accuracy for non-adjunct use of continuous glucose monitoring", Diabetes Technol. Ther., vol. 17, no. 3, pp. 1-10, 2015; B. P. Kovatchev, M. D. Breton, C. Cobelli et al., "Method, system and computer simulation environment for testing of monitoring and control strategies in diabetes", US Patent Application Publication, no. US2010/0179768A1; C. Dalla Man et al., "The UVA/PADOVA type 1diabetes simulator: new features", J Diabetes Sci. Technol., vol. 8, no. 1, pp. 26-34, 2014; R. Visentin et al., "Circadian variability of insulin sensitivity: Physiological input for in silico artificial pancreas", Diabetes Technol. Ther., vol. 17, no. 1, pp. 1-7, 2015; M. Vettoretti, A. Facchinetti, G. Sparacino and C. Cobelli, "A model of self-monitoring blood glucose measurement error: towards a simulator of diabetic patient therapeutics decisions", Diabetes Technol. Ther., vol. 17, no. S1, pp. A-165, 2015; A. Facchinetti et al., "Modeling the glucose sensor error", IEEE Trans. Biomed. Eng., vol. 61, no. 3, pp. 620-629, 2014; Diabetes Research In Children Network (DirecNet) Study Group, "Use of the DirecNet Applied Treatment Algorithm (DATA) for diabetes management with real-time continuous glucose monitoring (the FreeStyle Navigator)", Pediatrics Diabetes, vol. 9, pp. 147-147, 2008; JDRF CGM Study Group, "JDRF randomized clinical trial to assess the efficacy of real-time continuous glucose monitoring in the management of type 1 diabetes: research design and methods", Diabetes Technol. Ther., vol. 10, no. 4, pp. 310-321, 2008; J. Pettus, D. A. Price, and S. V. Edelman, "How patients with type 1 diabetes translate continuous glucose monitoring data into diabetes management decisions", Endocr. Pract., vol. 25, pp. 1-15, 2015; J. Burdik et al., "Missed insulin meal boluses and elevated haemoglobin A1c levels in children receiving insulin pump therapy", Pediatrics, vol. 113, no. 3, pp. e221-e224, 2004.

SUMMARY OF THE INVENTION

A comprehensive mathematical model of T1D patient decision-making usable to simulate, in silico, realistic glucose/insulin dynamics, for several days, in a variety of subjects who take therapeutic actions (e.g. insulin dosing) driven by either SMBG or CGM is provided. The mathematical model, hereafter referred to as decision-making (DM) model, can simulate many real-life situations and everyday patient behaviors. Accurate submodels of SMBG and CGM measurement errors are incorporated in the comprehensive DM model. Moreover, the DM model accounts for common errors the patients are used to doing in their diabetes management, such as miscalculations of meal carbohydrate content, early/delayed insulin administrations and missed insulin boluses.

The structure chosen for the comprehensive model, displayed in FIG. 1, is modular, i.e. composed by several interconnected blocks, each of them allowing different configurations depending on the specific therapy the user is interested in simulating. The DM model inputs are a simulation scenario, which comprises a sequence of meals carbohydrate content and information about physical exercise, and patient-specific parameters required for the calculation of the therapy. The simulator output is the patient glucose concentration. The DM model is composed by four blocks. The core block is a glucose-insulin model of T1D patient (block A, FIG. 1) that, given in input carbohydrate intake and insulin pump infusion rate, returns in output patient BG and IG profiles. SMBG/CGM measurements are simulated by a device for glucose monitoring model (block B, FIG. 1) by exploiting the BG/IG profile returned by the T1D patient model. Meal carbohydrate content and SMBG/CGM measurements are used by the T1D therapy model (block C, FIG. 1), which simulates the therapeutic decisions the patient takes in diabetes management to determine carbohydrate intake and insulin boluses. Finally, the insulin pump infusion rate is simulated by an insulin pump model (block D, FIG. 1).

In a first aspect, a system or method for modeling decision-making in managing type 1 diabetes is provided, comprising: a type 1 diabetes therapy model; a type 1 diabetes patient glucose-insulin system model; a device for glucose model; wherein, when a continuous glucose monitoring driven therapy is simulated, continuous glucose monitoring data are used to generate, in addition to pre-meal boluses, post-meal correction boluses in response to hyperglycemic alarms, to generate hypo-treatments in response to hypoglycemic alarms, to correct insulin boluses for continuous glucose monitoring trend/prediction, and to correct basal insulin for current blood glucose value/trend/prediction.

In an embodiment of the system or method of the first aspect, the system or method further comprises an insulin pump model, wherein the insulin pump model is configured to receive as input an insulin dose generated by the type 1 diabetes therapy model and configured to return as output an insulin pump infusion rate.

In an embodiment of the system or method of the first aspect, which is generally applicable (i.e., independently combinable with any of the aspects or embodiments identified herein), the type 1 diabetes patient glucose-insulin system model is configured to simulate the blood glucose and interstitial glucose concentration profiles in a type 1 diabetes patient resulting from carbohydrates intake and insulin pump infusions.

In an embodiment of the system or method of the first aspect, which is generally applicable (i.e., independently combinable with any of the aspects or embodiments identified herein), the type 1 diabetes patient glucose-insulin system model is configured to describe physiological events related to BG dynamics including gastrointestinal absorption of carbohydrates, insulin and glucagon kinetics and their action in regulating glucose endogenous production and utilization.

In an embodiment of the system or method of the first aspect, which is generally applicable (i.e., independently combinable with any of the aspects or embodiments identified herein), the type 1 diabetes patient glucose-insulin system model is configured to reproduce dynamics of a population of virtual patients, each patient represented by a set of model parameters, and to run multi-day simulations utilizing a description of inter-day and intra-day variability of insulin sensitivity.

In an embodiment of the system or method of the first aspect, which is generally applicable (i.e., independently combinable with any of the aspects or embodiments identified herein), the type 1 diabetes therapy model is configured to simulate therapeutic decisions that type 1 diabetes patients make on the basis of meal composition and blood glucose monitoring, including errors that patients make in diabetes management. Wherein the type 1 diabetes therapy model is configured to receive in input information about meal carbohydrate content and physical exercise, blood glucose measurements, and patient-specific therapy parameters, and wherein the type 1 diabetes therapy model is configured to return as output carbohydrate intake and insulin doses.

In an embodiment of the system or method of the first aspect, which is generally applicable (i.e., independently combinable with any of the aspects or embodiments identified herein), the type 1 diabetes therapy model is configured to simulate either a self-monitored blood glucose driven insulin therapy or a continuous glucose monitoring driven insulin therapy.

In an embodiment of the system or method of the first aspect, which is generally applicable (i.e., independently combinable with any of the aspects or embodiments identified herein), the device for glucose monitoring model is configured to generate glucose measurements used by patients in their diabetes management to adjust insulin doses or carbohydrate intake, and wherein the device for glucose monitoring model is configured to receive a glucose concentration as input and is configured to simulate self-monitored blood glucose spot measurements or a continuous glucose monitoring profile.

In a second aspect, a system or method for assessing whether a continuous glucose monitor is safe to employ in dosing insulin, the method accounting for intra-individual patient variability is provided, comprising: running, using a first decision-making module, simulations of insulin therapy driven by self-monitored blood glucose data and thereafter computing metrics values using virtual patient blood glucose profiles to assess a level of glycemic control; running, using a second decision-making module, simulations of insulin therapy driven by continuous glucose monitoring data and thereafter computing metrics values using virtual patient blood glucose profiles to assess a level of glycemic control; comparing the metrics values to determine if the use of the continuous glucose monitor is at least as safe as the use of self-monitored blood glucose for insulin dosing.

In an embodiment of the second aspect, which is generally applicable (i.e., independently combinable with any of the aspects or embodiments identified herein), the decision-making module utilizes a nonlinearized glucose-insulin model.

In an embodiment of the second aspect, which is generally applicable (i.e., independently combinable with any of the aspects or embodiments identified herein), the decision-making module is configured to run multi-day simulations, whereby time-variability of insulin sensitivity is accounted for.

In an embodiment of the second aspect, which is generally applicable (i.e., independently combinable with any of the aspects or embodiments identified herein), the decision-making module is configured to model a real patient's decision-making actions, taking into account possible errors made by patients in their diabetes management, wherein the errors include miscalculation of meal carbohydrate content, early insulin dose administration, delayed insulin dose administrations, and missed boluses occurrence.

In an embodiment of the second aspect, which is generally applicable (i.e., independently combinable with any of the aspects or embodiments identified herein), the decision-making module receives a simulation scenario as model inputs, the model inputs comprising a sequence of meals carbohydrate content, information about physical exercise, and patient-specific parameters required for the calculation of a therapy recommendation, and wherein the decision making module outputs a simulator output comprising a patient glucose concentration.

In an embodiment of the second aspect, which is generally applicable (i.e., independently combinable with any of the aspects or embodiments identified herein), the decision-making module utilizes models including: a glucose-insulin model of a type 1 diabetes patient, configured to receive as input carbohydrate intake and insulin pump infusion rate, and configured to return as output patient blood glucose and interstitial glucose profiles; a glucose monitoring model configured to simulate self-monitored blood glucose and continuous glucose monitor measurements utilizing the output of the glucose-insulin model; a type 1 diabetes therapy model configured to use meal carbohydrate content and self-monitored blood glucose and continuous glucose monitor measurements to simulate therapeutic decisions a patient makes in diabetes management to determine carbohydrate intake and insulin boluses; and an insulin pump model configured to simulate an insulin pump infusion rate.

In an embodiment of the second aspect, which is generally applicable (i.e., independently combinable with any of the aspects or embodiments identified herein), the system or method further comprises, if it is determined that the use of the continuous glucose monitor is at least as safe as the use of self-monitored blood glucose for insulin dosing, issuing insulin dosing instructions to an insulin pump by the continuous glucose monitor, whereby a patient receives an insulin dose.

In an embodiment of the second aspect, which is generally applicable (i.e., independently combinable with any of the aspects or embodiments identified herein), the patient has type 1 diabetes, and wherein improved glycemic control in type 1 diabetes management for the patient is obtained.

In an embodiment of the second aspect, which is generally applicable (i.e., independently combinable with any of the aspects or embodiments identified herein), the insulin dosing instructions are generated by: calculating, using a hypotreatment module, carbohydrate intake by adding to meal carbohydrate content hypotreatments, generated by a hypotreatment module; calculating, using a carb-counting module, a meal bolus before a meal to cover a meal carbohydrate intake; correcting, by the carb-counting module, a patient estimate of meal carbohydrate content by exploiting a model of patient carbohydrate counting error; calculating, using a meal bolus module, an insulin dose required to cover the meal using a patient carb ratio; and adding a correction insulin bolus to the meal bolus in order to take into account the patient's current glucose concentration.

In an embodiment of the second aspect, which is generally applicable (i.e., independently combinable with any of the aspects or embodiments identified herein), a bolus time variability module calculates a variability in the pre-meal bolus administration time, whereby an occurrence of early/delayed bolus administration is simulated.

In an embodiment of the second aspect, which is generally applicable (i.e., independently combinable with any of the aspects or embodiments identified herein), an occurrence of missed boluses is simulated by a missed bolus block.

In an embodiment of the second aspect, which is generally applicable (i.e., independently combinable with any of the aspects or embodiments identified herein), the insulin dose is calculated by adding to a basal insulin rate insulin bolus, and wherein the insulin dose is corrected, using a correction for exercise module, by using information about physical exercise.

In a third aspect, a system or method for providing a real-time therapeutic recommendation for use in type 1 diabetes management in a patient is provided, comprising: inputting, to a decision support module, data including continuous glucose monitoring data obtained from a glucose sensor, insulin pump data, and other diabetes management data; generating, based on the input data, a first therapeutic recommendation; displaying the therapeutic recommendation to a patient; inputting, to the decision support model, data indicative of an action taken by the patient in response to receiving the displayed therapeutic recommendation, the data including continuous glucose monitoring data obtained from the glucose sensor and insulin pump data; and generating, based on the input data and the data indicative of an action taken by the patient, a second therapeutic recommendation.

In an embodiment of the third aspect, which is generally applicable (i.e., independently combinable with any of the aspects or embodiments identified herein), the continuous glucose monitoring data is selected from the group consisting of a glucose concentration trend, a predicted glucose concentration, a number of past hyperglycemic events, and a number of past hypoglycemic events.

In an embodiment of the third aspect, which is generally applicable (i.e., independently combinable with any of the aspects or embodiments identified herein), the other diabetes management data is selected from the group consisting of meal data and physical exercise data.

In an embodiment of the third aspect, which is generally applicable (i.e., independently combinable with any of the aspects or embodiments identified herein), the first therapeutic recommendation or the second therapeutic recommendation is selected from the group consisting of a recommended insulin dose and a basal insulin change.

In an embodiment of the third aspect, which is generally applicable (i.e., independently combinable with any of the aspects or embodiments identified herein), the first or second therapeutic recommendation is delivered through a smartphone notification.

In an embodiment of the third aspect, which is generally applicable (i.e., independently combinable with any of the aspects or embodiments identified herein), the decision support module compares the data indicative of an action taken by the patient responsive to the first therapeutic recommendation to determine if the patient has taken the therapeutic recommendation, has ignored the therapeutic recommendation, or has taken an action similar to the therapeutic recommendation.

In an embodiment of the third aspect, which is generally applicable (i.e., independently combinable with any of the aspects or embodiments identified herein), the action taken by the patient is employed to modify a decision-making module configured to simulate real-life situations and everyday patient behaviors, wherein the decision-making module utilizes self-monitored blood glucose data measurement errors, continuous glucose monitoring data measurement errors, miscalculations of meal carbohydrate content, early insulin administration errors, delayed insulin administration errors, and missed insulin bolus errors.

In an embodiment of the third aspect, which is generally applicable (i.e., independently combinable with any of the aspects or embodiments identified herein), the decision-making module utilizes patient data to assess glycemic control or efficacy of the decision support module, or to suggest modifications to the decision support module to improve its performance.

In a fourth aspect, a system or method for delivering a therapeutic recommendation for insulin delivery is provided, comprising: collecting data from a patient over a period of time, the data including continuous glucose monitoring data obtained from a glucose sensor and insulin pump data; generating, based on the collected data, a model comprising estimated parameters of the patient's physiology that reproduces the patient's glucose-insulin dynamics; inputting the estimated parameters into a type 1 diabetes patient glucose-insulin model, whereby an individualized patient model is obtained; utilizing the individualized patient model in patient-specific simulations to estimate optimal insulin therapy parameters or individualized guidelines for continuous glucose monitoring-driven insulin dosing; and outputting the optimal insulin therapy parameters.

In an embodiment of the fourth aspect, which is generally applicable (i.e., independently combinable with any of the aspects or embodiments identified herein), outputting the optimal insulin therapy parameters comprises displaying the therapeutic recommendation to a patient on a display.

In an embodiment of the fourth aspect, which is generally applicable (i.e., independently combinable with any of the aspects or embodiments identified herein), the display is a smartphone display.

In an embodiment of the fourth aspect, which is generally applicable (i.e., independently combinable with any of the aspects or embodiments identified herein), outputting the optimal insulin therapy parameters comprises issuing instructions to an insulin pump for delivering an insulin dose.

In an embodiment of the fourth aspect, which is generally applicable (i.e., independently combinable with any of the aspects or embodiments identified herein), utilizing the individualized patient model in patient-specific simulations comprises iteratively running simulations, wherein at the first iteration, the patient's current insulin therapy is implemented, then, at each subsequent iteration, the therapy parameters are updated until it is determined that the therapy parameters satisfy predetermined criteria.

In an embodiment of the fourth aspect, which is generally applicable (i.e., independently combinable with any of the aspects or embodiments identified herein), it is determined if the therapy parameters need to be updated by assessing a level of glycemic control.

Any of the features of an embodiment of the first through fourth aspects is applicable to all aspects and embodiments identified herein. Moreover, any of the features of an embodiment of the first through fourth aspects is independently combinable, partly or wholly with other embodiments described herein in any way, e.g., one, two, or three or more embodiments may be combinable in whole or in part. Further, any of the features of an embodiment of the first through fourth aspects may be made optional to other aspects or embodiments. Any aspect or embodiment of a method can be performed by a system or apparatus of any aspect or embodiment, and any aspect or embodiment of a system can be configured to perform a method of any aspect or embodiment.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE PREFERRED EMBODIMENT

Figure 1:
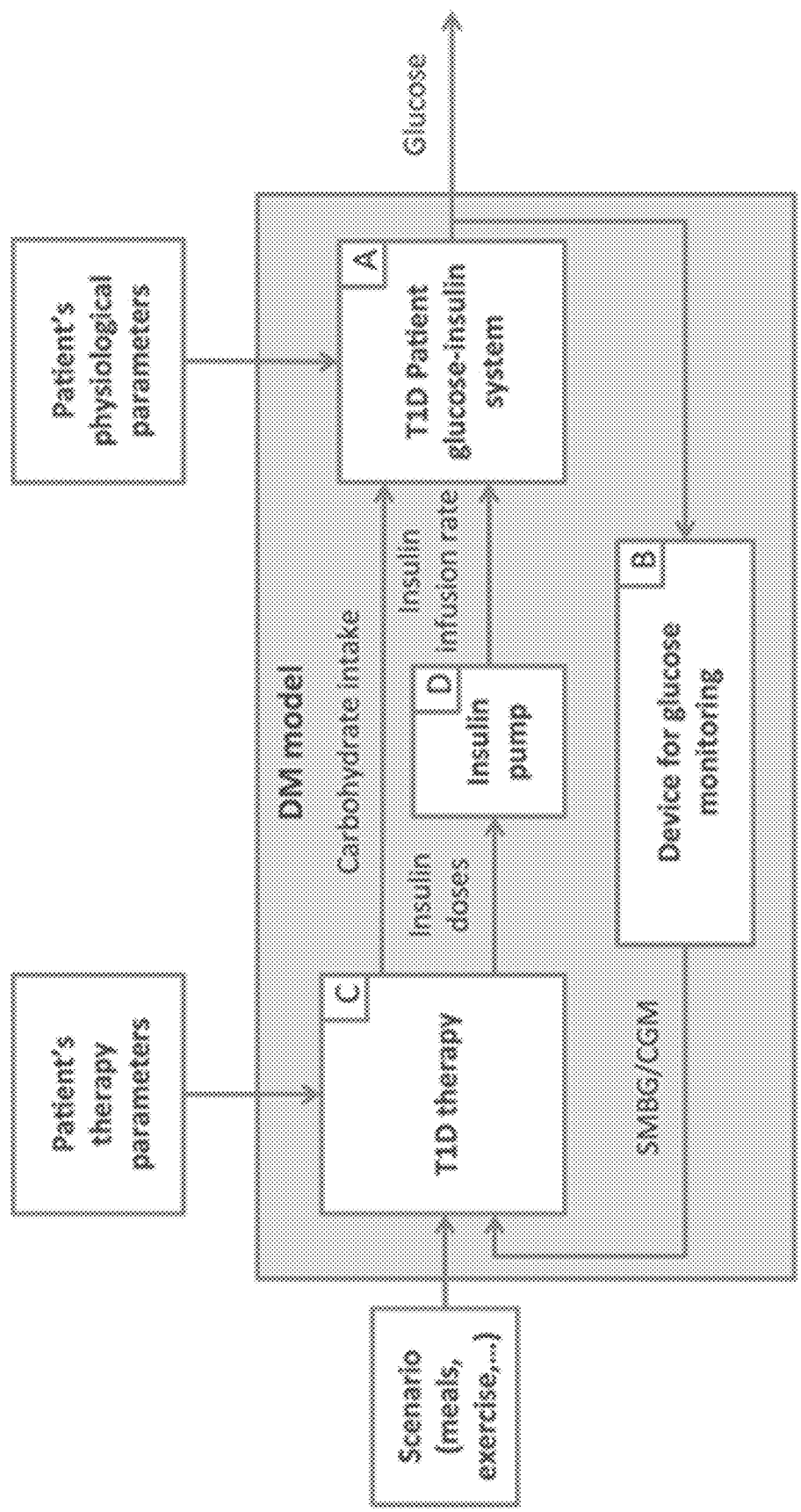
FIG. 1 is a block diagram of a general structure of the DM model whose main components are labelled with letters A, B, C and D.

An embodiment is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

In the four subsections, A to D below, the four components of the DM model are described in detail.

T1D Patient Submodel

This submodel (block A, FIG. 1) simulate the BG and IG concentration profiles in a T1D patient resulting from carbohydrates intake and insulin pump infusions. In a preferred embodiment, a model of T1D patient glucose-insulin system can be used, which received FDA approval to substitute preclinical trials for certain insulin treatments. In particular, the T1D patient glucose-insulin model describes physiological events related to BG dynamics like gastrointestinal absorption of carbohydrates, insulin and glucagon kinetics and their action in regulating glucose endogenous production and utilization. The model can reproduce the dynamics of a large population of virtual patients (each one represented by a set of model parameters) and run multi-day simulations thanks to the description of inter- and intra-day variability of insulin sensitivity.

Device for Glucose Monitoring Submodel

The device for glucose monitoring submodel (block B of FIG. 1) generates the glucose measurements used by patients in their diabetes management to adjust insulin doses or carbohydrate intake. The model receives the glucose concentration (BG or IG) in input and can be configured to simulate SMBG spot measurements or CGM profile. When a SMBG driven therapy is simulated, the device for glucose monitoring model produces sparse BG measurements obtained by down sampling the BG profile and corrupting samples by using a model of SMBG measurement error. In a preferred embodiment, a stochastic model of general applicability can be employed, whose parameters can be tuned to reproduce measurements collected by different commercial SMBG devices. When a CGM driven therapy is simulated, the device for glucose monitoring model generates a continuous-time signal obtained by corrupting the IG profile by using a model of CGM measurement error. In a preferred embodiment, a multi-component model of general applicability can be employed, whose parameters can be tuned to reproduce measurements collected by different commercial CGM devices.

T1D Therapy Submodel

The T1D therapy submodel (block C in FIG. 1) simulates the therapeutic decisions that T1D patients make in their everyday life on the basis of meal composition and BG monitoring. To simulate realistic patient behavior, the model includes the principal common errors that patients are used to doing in their diabetes management. The model receives in input information about meal carbohydrate content and physical exercise, BG measurements (either CGM or SMBG) and patient-specific therapy parameters. The model returns in output carbohydrate intake (both meals and other carbohydrate consumptions) and insulin doses. The T1D therapy model can be configured to simulate either a SMBG-driven insulin therapy or a CGM-driven insulin therapy.

In a preferred embodiment, when an SMBG driven therapy is simulated, carbohydrate intake is calculated by adding to the meal carbohydrate content hypotreatments, i.e. adjunctive carbohydrate intakes (e.g. snacks of 15-20 grams) necessary to resolve hypoglycemic events; pre-meal insulin boluses are computed before meals to cover meal carbohydrate intake on the basis of an estimate of meal carbohydrate content and current BG concentration.

When a CGM driven therapy is simulated, CGM data are used to generate, besides pre-meal boluses, post-meal correction boluses in response to hyperglycemic alarms, to generate hypo-treatments in response to hypoglycemic alarms, to correct insulin boluses for CGM trend/prediction and to correct basal insulin for current BG value/trend/prediction.

Insulin Pump Submodel

The insulin pump model (block D in FIG. 1) is simply an actuator that receives in input insulin doses generated by the T1D therapy model and returns in output the insulin pump infusion rate (e.g. in mmol/min). A parameter of the model is the duration of insulin boluses infusion.

Aspects of Methods and Systems

The methods and systems described herein provide various advantages and improvements over state-of-art methods and systems.

First, the methods or systems include a model of patient decision-making (DM), i.e. the complex process in which diabetic patients in their every-day life analyze glucose monitoring data and take therapeutic decisions (e.g. insulin dosing). In particular, the DM model takes into account possible errors the patients are used to doing in their diabetes management e.g. miscalculation of meal carbohydrate content, early/delayed insulin doses administrations and missed boluses occurrence. Such components, linked to patient's behavior and not considered by previous simulation approaches, are key to obtaining a realistic simulation scenario and test SMBG/CGM driven therapy strategies in a nearly real-life context.

Second, the embodiments are based on a realistic complex non-linear model of T1D patient glucose-insulin dynamics, which allows a better description of patient physiology than the simplified models used in conventional methods. In addition, the used glucose-insulin model allows running multi-day simulations (not possible with conventional methods) thanks to the description of inter- and intra-day variability of insulin sensitivity.

Finally, the modular structure of the embodiments allows a great number of configurations that can be used for many applications involving in silico testing of T1D therapies using realistic models of commercial SMBG and CGM in a wide population of virtual subject in which intra- and inter-day variability is properly considered.

Applications

In the following subsections, four possible applications of the comprehensive DM model are presented i.e. the use of the DM model to assess in silico if/when CGM can safely substitute SMBG in T1D management, to develop and test candidate guidelines for CGM driven insulin dosing, to optimize and individualize off-line insulin therapies and to develop and test decision support systems.

1. Assessment of Non-Adjunct Use of CGM

Figure 2:
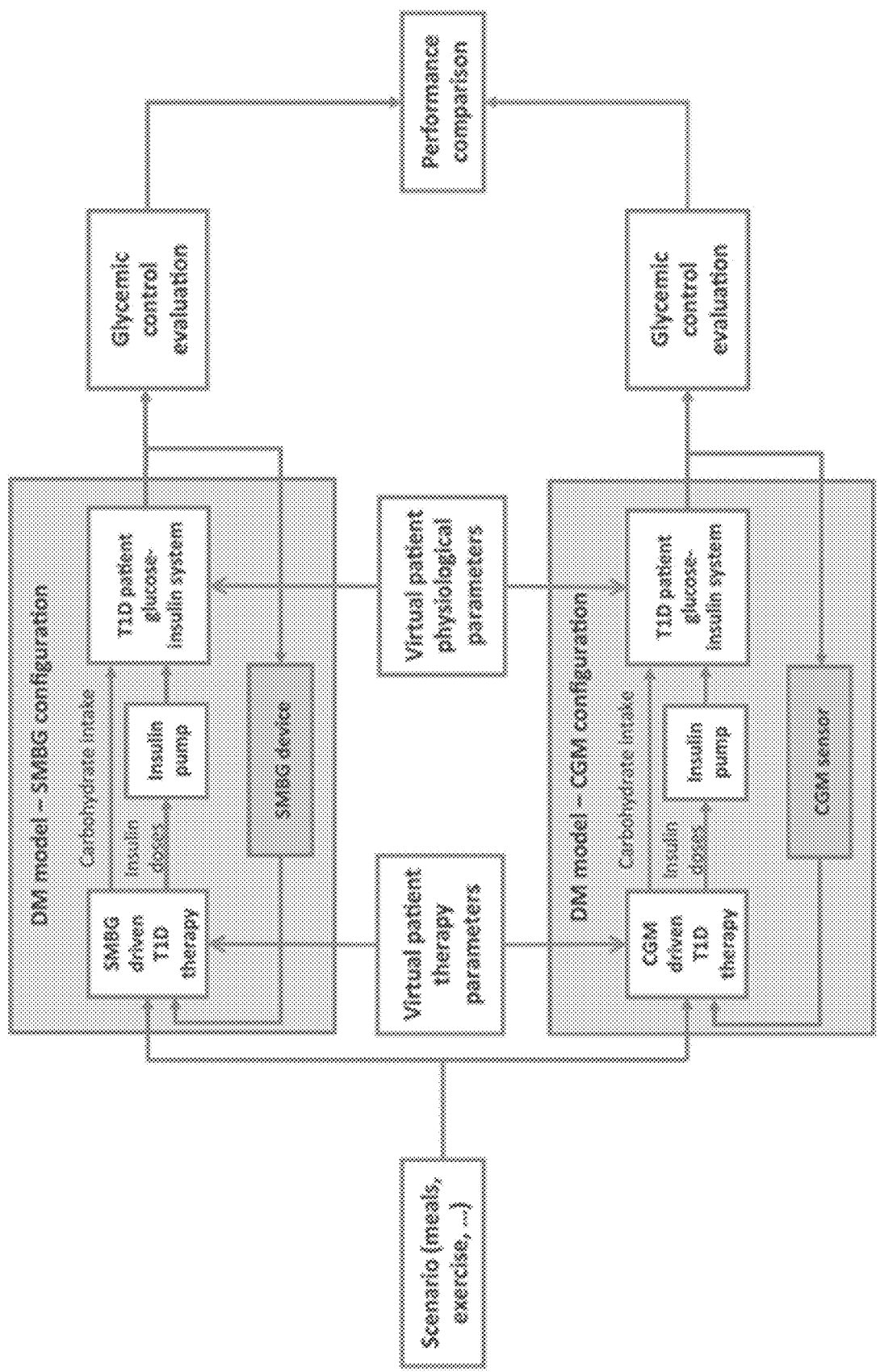
FIG. 2 is a block diagram of an application of the DM model to test and compare in silico SMBG- and CGM-driven T1D therapies.

A direct application of the DM model is its use to test in silico if CGM can safely substitute SMBG in diabetes management. For such a purpose, the DM model can be employed as represented in FIG. 2. In particular, several days simulations can be run in a large set of virtual patients by using two versions of the DM model: a first version configured to simulate SMBG driven insulin therapy (top model in FIG. 2) and a second version configured to simulate CGM driven insulin therapy (bottom model in FIG. 2). After simulation, virtual patient BG profiles can be used to assess the level of glycemic control achieved by the computation of a number of metrics. Finally, by comparing the metrics values obtained by the SMBG and the CGM configuration it can be determined if/when the use of CGM is as safe as SMBG for insulin dosing and if/when the use of CGM can even improve glycemic control in T1D management.

Simulations comparing the efficacy of SMBG and CGM driven T1D therapies were run by two embodiments of the DM model: embodiment A in which a SMBG driven therapy is simulated and embodiment B in which a CGM driven therapy is simulated. For both the embodiments in block A a model as described elsewhere herein is used. Concerning block B, in embodiment A a model of SMBG error derived for the One Touch Ultra 2 (Lifescan Inc., Milpitas, Calif.) is used, in embodiment B a model of the CGM sensor derived for the Dexcom G4 Platinum (Dexcom Inc., San Diego, Calif.) is used. The detailed structure for the T1D therapy model in embodiments A and B is reported in FIG. 3. Specifically, a single scheme is reported in which white blocks are activated both in embodiments A and B, while yellow blocks are activated in embodiment B only.

Figure 3:
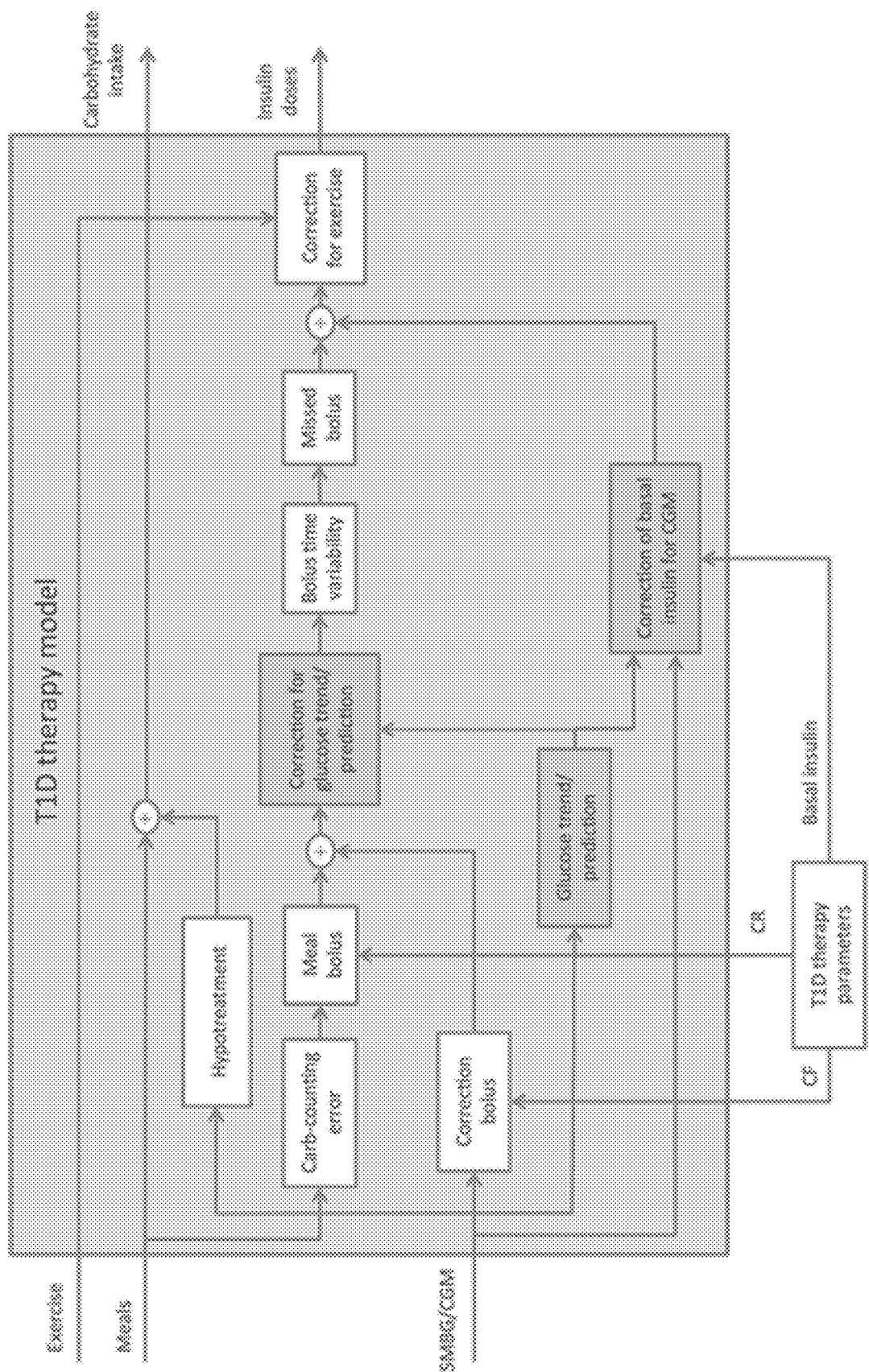
FIG. 3 is a block diagram of a possible embodiment of the T1D therapy model. White blocks are activated in both SMBG- and CGM-driven therapies, while blocks highlighted in yellow are activated only in CGM-driven therapies.

In both the embodiments, carbohydrate intake is calculated by adding to the meal carbohydrate content hypo-treatments, generated by the hypo-treatment block in FIG. 3.

Meal boluses are computed before meals to cover meal carbohydrate intake. The carb-counting block in FIG. 3 simulates patient estimate of meal carbohydrate content by exploiting a model of patient carbohydrate counting error. In this embodiment carb-counting errors (in %) are simulated by a normal distribution with zero mean and 20% standard deviation. The estimate of meal carbohydrate content is then used to calculate the insulin dose required to cover the meal. The computation is performed by the meal bolus block of FIG. 3 by using patient carb ratio (CR) according to the guidelines.

A correction insulin bolus is added to meal bolus in order to take into account patient current BG concentration. The correction bolus block in FIG. 3 calculates correction boluses by using patient correction factor (CF) and current BG measurement (collected by either SMBG or CGM).

Variability in the pre-meal bolus administration time is generated by the bolus time variability block in FIG. 3 to simulate the occurrence of early/delayed bolus administrations due to unexpected setbacks that may happen in real life. In this specific embodiment, pre-meal boluses time is sampled from a uniform distribution in the interval between 10 min before and 10 min after the meal beginning.

From time to time, the occurrence of missed boluses, regarded the major cause of suboptimal glycemic control, is simulated by the missed bolus block of FIG. 3. Despite the missed bolus block has been included in the general scheme of the embodiment, to obtain the preliminary results presented in the current file the occurrence of missed boluses has not been simulated.

The final insulin dose is calculated by adding to basal insulin rate (mmol/min) insulin boluses.

Final insulin doses are corrected by using information about physical exercise by the correction for exercise block of FIG. 3. Despite the correction for exercise block has been included in the general scheme of the embodiment, to obtain the preliminary results presented in the current file such a correction has not been simulated.

Insulin therapy parameters, CR and CF, as well as the basal insulin infusion rate used in the pump model are calculated from patient body weight and total daily insulin according to guidelines.

In embodiment A: 16-gram hypo-treatments are generated every 15 min whenever BG drops below 40 mg/dl, which is assumed to be the threshold at which hypoglycemia symptoms start appearing, until the BG returns inside the euglycemic range.

In embodiment B: 16-gram hypo-treatments are generated every 30 minutes when BG drops below 70 mg/dl, which is assumed to be the CGM hypoglycemic alarm threshold, until the CGM profile returns inside the euglycemic range.

Post-meal correction boluses are generated, besides pre-meal boluses, when CGM increases over 180 mg/dl, that is assumed to be the CGM hyperglycemic alarm threshold, and at least 2 hours passed since last insulin bolus. Post-meal correction boluses are generated as pre-meal correction boluses dividing the dose by two as an empirical way to account for insulin on board.

Both pre-meal and post-meal insulin boluses are adjusted to account for glucose trend/prediction calculated in real-time from the CGM profile by the glucose trend/prediction block in FIG. 3. The block labelled as correction for glucose trend/prediction in FIG. 3 adjusts the total insulin bolus (sum of meal and correction bolus) according to CGM trend/prediction. Since CGM has not been approved for insulin dosing yet, currently there are no officially approved guidelines to adjust insulin doses on the basis of CGM trend/prediction. In the literature, only two CGM trials are available in which specific instructions were given to patients on how to adjust their insulin doses on the basis of CGM trend, e.g., the DirectNet and the Juvenile Diabetes Research Foundation studies. Both these studies recommended to increase/decrease the insulin dose by 10% in response to a moderately increasing/decreasing CGM trend and to increase/decrease the insulin dose by 20% in response to a more rapidly increasing/decreasing CGM trend. These guidelines are adopted to implement the correction for glucose trend/prediction block in this embodiment.

Basal insulin infusion rate is corrected to account for current CGM value/trend/prediction by the correction of basal insulin for CGM block, whose function is to suspend basal insulin delivery when patient CGM profile is (or is going to be) below a certain level. Despite the correction of basal insulin for CGM block has been included in the general scheme of the embodiment, to obtain the preliminary results presented in the current file such a correction has not been simulated.

Finally, concerning the insulin pump model implementation, the duration of insulin boluses has been set to 1 minute.

Examples of Results

Figure 4:
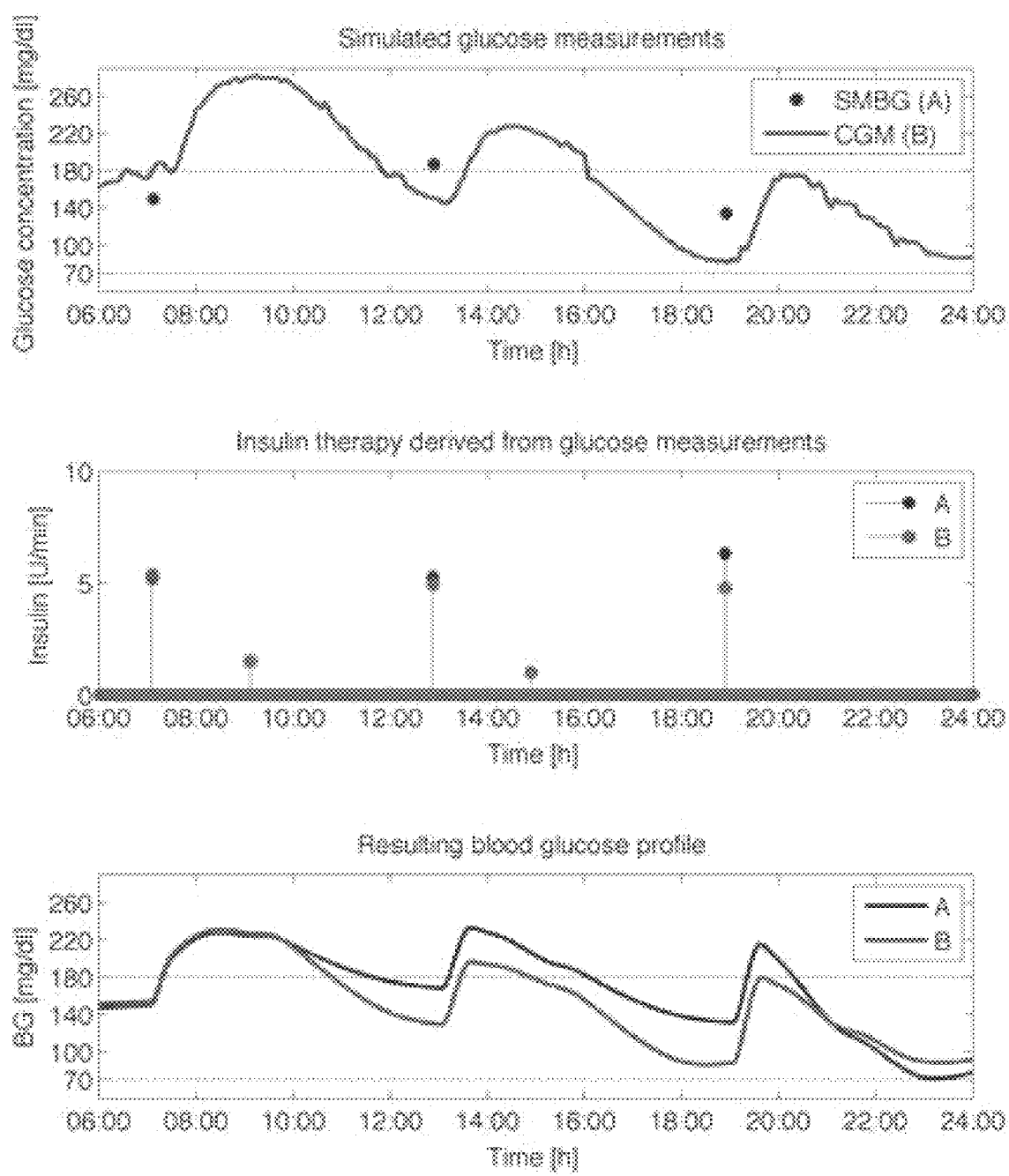
FIG. 4 includes several graphs showing comparison of results obtained by embodiments A and B in a representative subject. Top panel: SMBG samples (black circles) and CGM profile (blue line), used for insulin dosing respectively in embodiments A and B. Middle panel: insulin doses obtained by embodiments A (black circles) and B (blue circles). Bottom panel: BG profile obtained from the therapy of embodiment A (black line) compared with that obtained as result of the therapy of embodiment B (blue line).

Simulations were run in 20 adult virtual subjects for a 7-day period by using the DM model with both embodiment A and B. Each virtual subject has been associated to a specific scenario, which is the same used for embodiment A and B, containing three meals per day sampled from normal distributions with mean equal respectively to 60 grams for breakfast, 50 grams for lunch, and 70 grams for dinner, and CV equal to 20%. After simulation, the BG profiles obtained in each virtual subject for embodiments A and B have been compared. In FIG. 4, an example in which a better a glycemic control was achieved by the use of CGM (embodiment B) is reported. In particular, the post-meal correction boluses, that were administered at 09:00 and 15:00 as reaction to the CGM hyperglycemic alarms generated by CGM profile hyperglycemic threshold crossing, allow to reduce the time spent in hyperglycemia in embodiment B compared with embodiment A. For each virtual subject, the simulated BG profile was used to calculate, both in embodiments A and B, time-in-target, time-in-hypo and time-in-hyper, i.e. the percentage of samples falling respectively between 70 mg/dl and 180 mg/dl, under 70 mg/dl and over 180 mg/dl. In Table 1, the median values calculated for time-in-target, time-in-hypo and time-in-range in the 20 subjects are reported for embodiment A (second column) and B (third column). In embodiment B, compared with embodiment A, time-in-target significantly increases, from 60.04% to 69.05%, time-in-hyper significantly decreases, from 39.32% to 30.65%, while time-in-hypo slightly increases from 0.39% to 0.63%. To assess differences between metrics median values in embodiment A and B, a non-parametric paired sign test, whose p-values are reported in the fourth column of Table 1, was performed. With a 5% significance level, the improvement obtained in embodiment B for time-in-target and time-in-hyper is statistically significant, while the difference observed for time-in-hypo is not statistically significant.

TABLE 1

| Metric | Embodiment A | Embodiment B | P-value |
| --- | --- | --- | --- |
| Time-in-target | 60.04% | 69.05% | 0.0026 |
| Time-in-hypo | 0.39% | 0.63% | 0.7905 |
| Time-in-hyper | 39.32% | 30.65% | 0.0118 |

Table 1: Median values of time-in-target, time-in-hypo and time-in-hyper obtained for the glucose profiles simulated by model embodiments A and B are reported respectively in the second and third columns. P-values of a non-parametric paired sign test performed to compare metrics median values in embodiments A and B are reported in the fourth column.

2. Optimization of Guidelines for CGM-Driven Insulin Dosing

Figure 5:
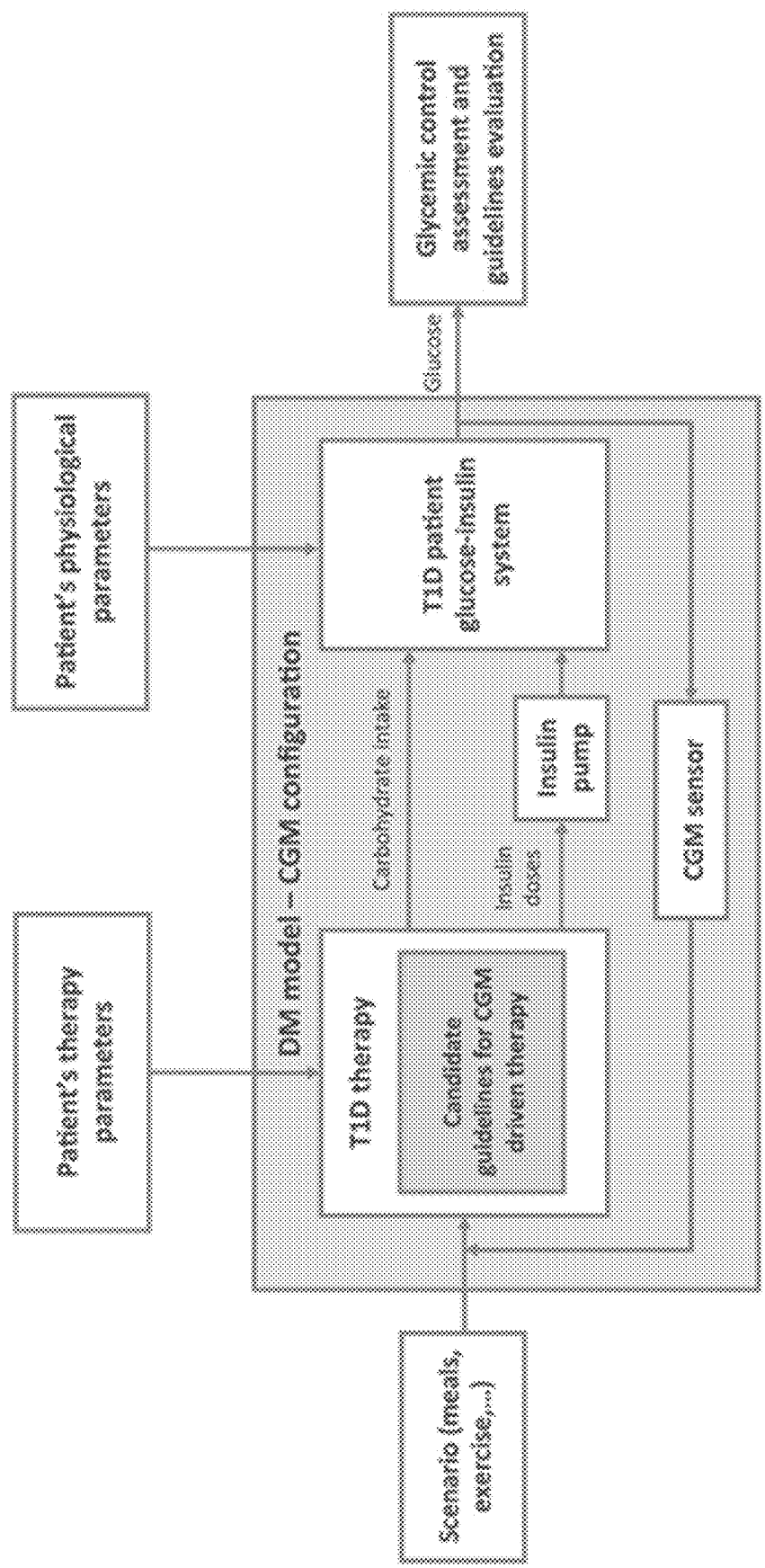
FIG. 5 is a block diagram of an application of the DM model to test and compare candidate guidelines for CGM-driven insulin therapy.

Currently, since CGM sensor has not been approved yet by regulatory agencies for insulin dosing, there are no officially approved guidelines for CGM driven insulin dosing. The DirectNet and the Juvenile Diabetes Research Foundation studies provide some non-officially approved guidelines to adjust insulin doses according to CGM trend. However, a recent survey revealed that patients use CGM trend to make significantly larger adjustment to insulin doses. The DM model can be an important tool to test and compare in silico candidate guidelines for CGM driven insulin dosing. For such a purpose, the DM model can be employed as represented in FIG. 5. Specifically, after defining a specific scenario, simulations can be run in a wide set of virtual patients by using a CGM configuration of the DM model in which block B simulates a certain CGM sensor device, and the T1D therapy model implements a set of candidate guidelines for CGM driven insulin dosing. These guidelines may include rules to adjust both insulin boluses and basal infusion rate according to CGM trend or prediction. The glycemic control achieved by each candidate guidelines can be assessed by a number of performance metrics in order to determine the safest rules that patients can use to calculate insulin doses on the basis of CGM readings. Candidate guidelines can be tested in the whole population of virtual patients or in a specific class of subjects (e.g. patients with low/high insulin sensitivity) to determine which are the best guidelines for each class of subjects.

3. Off-Line Insulin Therapy Optimization

Figure 6:
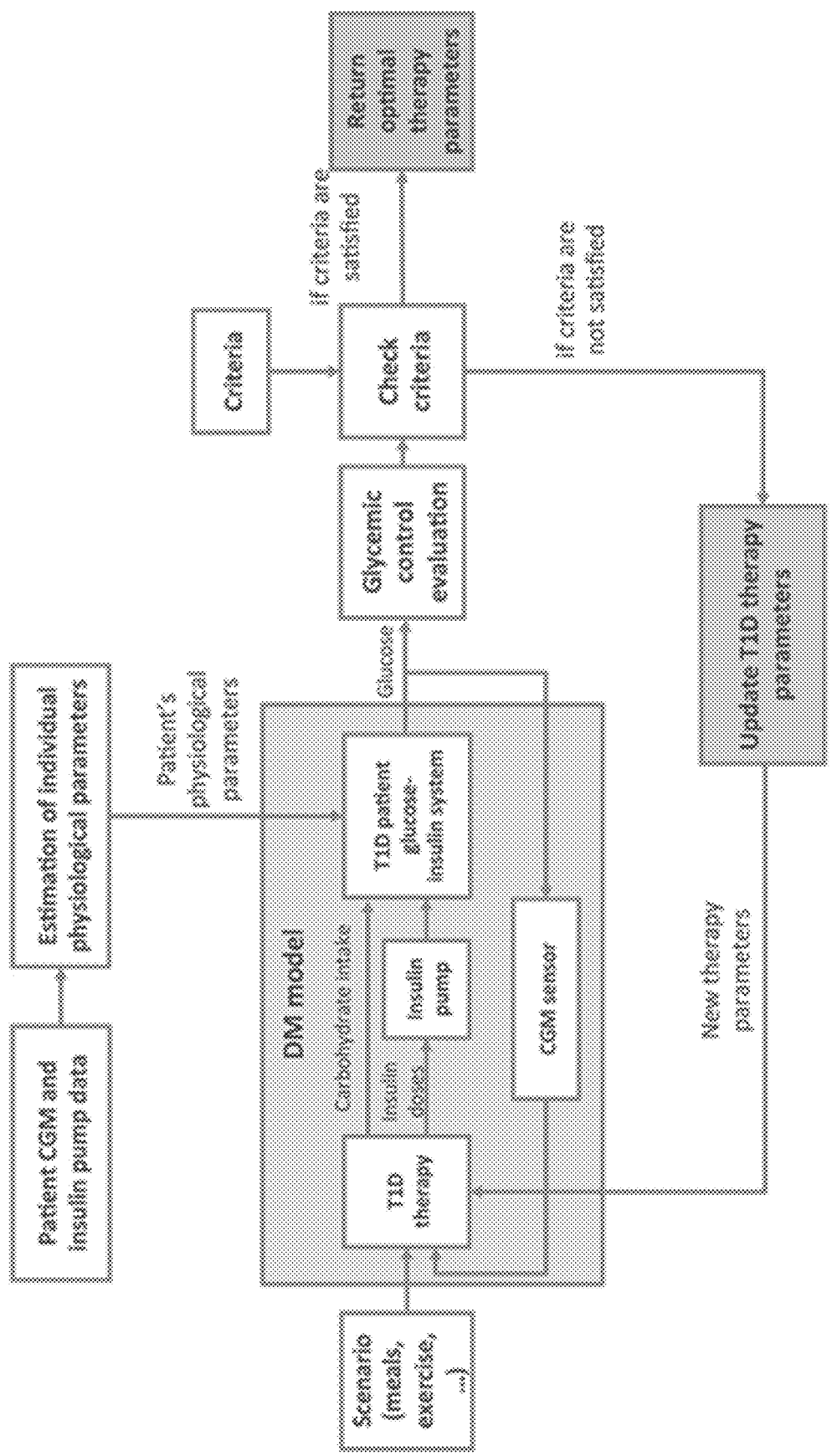
FIG. 6 is a block diagram of an application of the DM to off-line optimization of individualized insulin therapies.

The use of the DM model for off-line insulin therapy optimization is represented in FIG. 6. CGM and insulin pump data collected (e.g. in a week) for a specific patient can be employed to clone the specific patient's physiology i.e.

identify the parameters of the T1D patient model that allow reproducing that patient glucose-insulin dynamics. The estimated parameters of patient's physiology are then put into the T1D patient glucose-insulin model to obtain an individualized patient model. Such a model is included in the DM model and used to run patient-specific simulations in order to optimize patient insulin therapy, thus to estimate optimal insulin therapy parameters (e.g. CR, CF and basal insulin) and individualize guidelines for CGM driven insulin dosing. More specifically, after defining a specific scenario, simulations are run iteratively in order to optimize block C parameters. At the first iteration, the patient current insulin therapy is implemented in block C. Then, at each iteration, therapy parameters are updated until optimal parameters are found and returned in output. At each iteration, to determine if therapy parameters need to be updated or not, the level of glycemic control is assessed by some metrics and some glycemic control criteria are checked. If the performance of the current iteration therapy parameters satisfies the desired criteria, then the algorithm stops and returns in output optimal therapy parameters. Conversely, if the performance of the current iteration therapy parameters does not satisfy the desired criteria, then therapy parameters are updated and another iteration is performed.

4. Development of Algorithms for On-Line Decision Support

Figure 7:
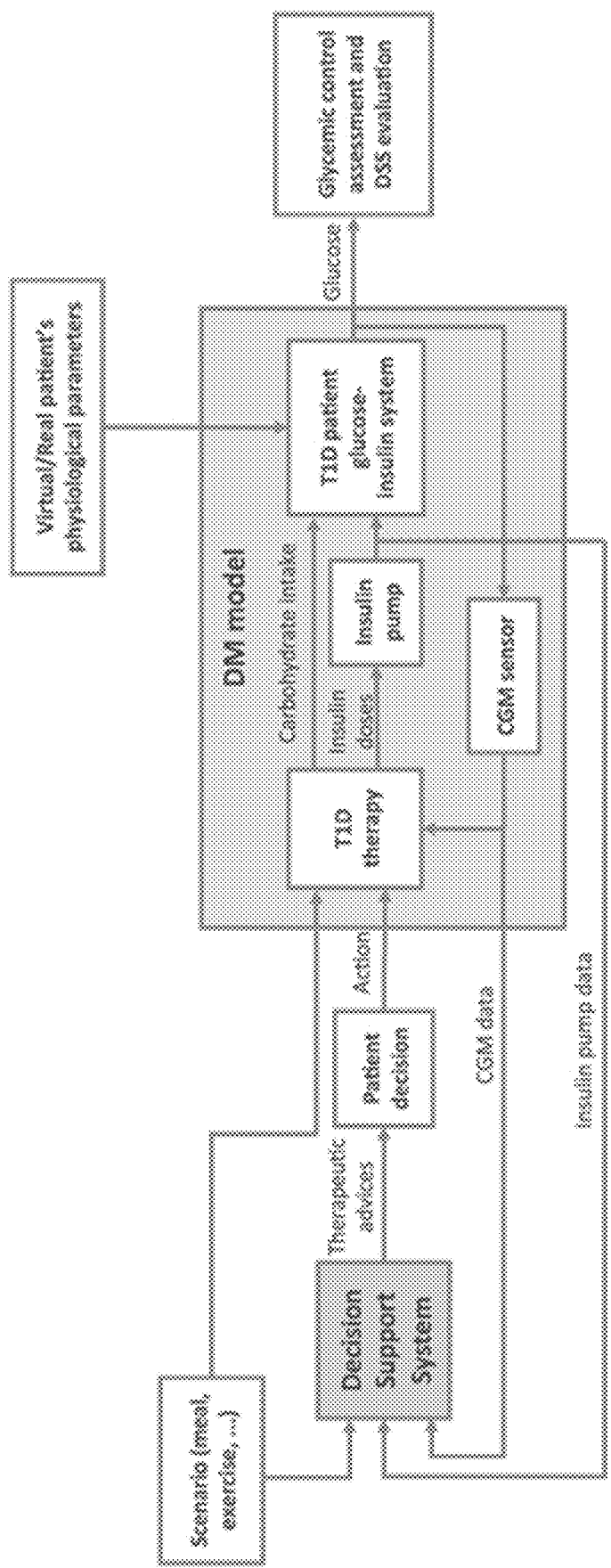
FIG. 7 is a block diagram of an application of the DM model to test and compare CGM-driven decision-support systems.

The DM model can be used to develop and test algorithms for on-line CGM-driven decision support i.e. smartphone applications which exploit insulin pump and CGM information (e.g. CGM trend, predicted glucose, number of past hyper/hypoglycemic events etc.) and other information (e.g. meals and physical exercise) to provide in real-time to the patient therapeutic recommendations (e.g. recommended insulin dose, basal insulin changes etc.). A possible use of the DM model for such a purpose is represented in FIG. 7. A candidate decision support system (DSS), highlighted in yellow, is given in input information about the current scenario (e.g. meals and physical exercise) and CGM and insulin pump data simulated by the DM model. The DSS analyzes data and returns in output some recommendations about changes/adjustments to patient's therapy. When the patient receives the recommendations, e.g. through a smartphone notification if the decision support algorithm is implemented in a smartphone, he/she can decide to accept the advice and take the recommended action, ignore the advice or accept the advice and take an action similar to the recommended one (e.g. stronger/weaker). Patient's decision is modelled by the block patient decision in FIG. 7 that receives in input the DSS recommendations and returns in output the actual actions the patient takes which are then used to modify the therapy implemented in the block C of the DM model. Simulations with the whole model of FIG. 7 allow generation of BG profiles of patients who take their therapeutic decisions taking advantage of a particular DSS recommendations. A final evaluation of the level of glycemic control achieved permits evaluating the DSS performance and suggests if/how the decision support algorithm can be modified to improve its performance.

Methods and Systems

System 1. A system for modeling decision-making in managing type 1 diabetes, comprising: a type 1 diabetes therapy model; a type 1 diabetes patient glucose-insulin system model; a device for glucose model; wherein, when a continuous glucose monitoring driven therapy is simulated, continuous glucose monitoring data are used to generate, in addition to pre-meal boluses, post-meal correction boluses in response to hyperglycemic alarms, to generate hypoglycemic treatments in response to hypoglycemic alarms, to correct insulin boluses for continuous glucose monitoring trend/prediction, and to correct basal insulin for current blood glucose value/trend/prediction.

System 2. The system of System 1, further comprising an insulin pump model, wherein the insulin pump model is configured to receive as input an insulin dose generated by the type 1 diabetes therapy model and configured to return as output an insulin pump infusion rate.

System 3. The system any one of Systems 1 to 2, wherein the type 1 diabetes patient glucose-insulin system model is configured to simulate the blood glucose and interstitial glucose concentration profiles in a type 1 diabetes patient resulting from carbohydrates intake and insulin pump infusions.

System 4. The system any one of Systems 1 to 3, wherein the type 1 diabetes patient glucose-insulin system model is configured to describes physiological events related to BG dynamics including gastrointestinal absorption of carbohydrates, insulin and glucagon kinetics and their action in regulating glucose endogenous production and utilization.

System 5. The system any one of Systems 1 to 4, wherein the type 1 diabetes patient glucose-insulin system model is configured to reproduce dynamics of a population of virtual patients, each patient represented by a set of model parameters, and to run multi-day simulations utilizing a description of inter-day and intra-day variability of insulin sensitivity.

System 6. The system any one of Systems 1 to 5, wherein the type 1 diabetes therapy model is configured to simulate therapeutic decisions that type 1 diabetes patients make on the basis of meal composition and blood glucose monitoring, including errors that patients make in diabetes management. Wherein the type 1 diabetes therapy model is configured to receive in input information about meal carbohydrate content and physical exercise, blood glucose measurements, and patient-specific therapy parameters, and wherein the type 1 diabetes therapy model is configured to return as output carbohydrate intake and insulin doses.

System 7. The system any one of Systems 1 to 6, wherein the type 1 diabetes therapy model is configured to simulate either a self-monitored blood glucose driven insulin therapy or a continuous glucose monitoring driven insulin therapy.

System 8. The system any one of Systems 1 to 7, wherein the device for glucose monitoring model is configured to generate glucose measurements used by patients in their diabetes management to adjust insulin doses or carbohydrate intake, and wherein the device for glucose monitoring model is configured to receive a glucose concentration as input and is configured to simulate self-monitored blood glucose spot measurements or a continuous glucose monitoring profile.

Method 9. A method for assessing whether a continuous glucose monitor is safe to employ in dosing insulin, the method accounting for intra-individual patient variability, comprising: running, using a first decision-making module, simulations of insulin therapy driven by self-monitored blood glucose data and thereafter computing metrics values using virtual patient blood glucose profiles to assess a level of glycemic control; running, using a second decision-making module, simulations of insulin therapy driven by continuous glucose monitoring data and thereafter computing metrics values using virtual patient blood glucose profiles to assess a level of glycemic control; comparing the metrics values to determine if the use of the continuous glucose monitor is at least as safe as the use of self-monitored blood glucose for insulin dosing.

Method 10. The method of Method 9, wherein the decision-making module utilizes a nonlinearized glucose-insulin model.

Method 11. The method of any one of Methods 9 to 10, wherein the decision-making module is configured to run multi-day simulations, whereby time-variability of insulin sensitivity is accounted for.

Method 12. The method of any one of Methods 9 to 11, wherein the decision-making module is configured to model a real patient's decision-making actions, taking into account possible errors made by patients in their diabetes management, wherein the errors include miscalculation of meal carbohydrate content, early insulin dose administration, delayed insulin dose administrations, and missed boluses occurrence.

Method 13. The method of any one of Methods 9 to 12, wherein the decision-making module receives a simulation scenario as model inputs, the model inputs comprising a sequence of meals carbohydrate content, information about physical exercise, and patient-specific parameters required for the calculation of a therapy recommendation, and wherein the decision making module outputs a simulator output comprising a patient glucose concentration.

Method 14. The method of any one of Methods 9 to 13, wherein the decision-making module utilizes models including: a glucose-insulin model of a type 1 diabetes patient, configured to receive as input carbohydrate intake and insulin pump infusion rate, and configured to return as output patient blood glucose and interstitial glucose profiles; a glucose monitoring model configured to simulate self-monitored blood glucose and continuous glucose monitor measurements utilizing the output of the glucose-insulin model; a type 1 diabetes therapy model configured to use meal carbohydrate content and self-monitored blood glucose and continuous glucose monitor measurements to simulate therapeutic decisions a patient makes in diabetes management to determine carbohydrate intake and insulin boluses; and an insulin pump model configured to simulate an insulin pump infusion rate.

Method 15. The method of any one of Methods 9 to 14, further comprising, if it is determined that the use of the continuous glucose monitor is at least as safe as the use of self-monitored blood glucose for insulin dosing, issuing insulin dosing instructions to an insulin pump by the continuous glucose monitor, whereby a patient receives an insulin dose.

Method 16. The method of any one of Methods 9 to 15, wherein the patient has type 1 diabetes, and wherein improved glycemic control in type 1 diabetes management for the patient is obtained.

Method 17. The method of any one of Methods 9 to 16, wherein the insulin dosing instructions are generated by: calculating, using a hypotreatment module, carbohydrate intake by adding to meal carbohydrate content hypotreatments, generated by a hypotreatment module; calculating, using a carb-counting module, a meal bolus before a meal to cover a meal carbohydrate intake; correcting, by the carb-counting module, a patient estimate of meal carbohydrate content by exploiting a model of patient carbohydrate counting error; calculating, using a meal bolus module, an insulin dose required to cover the meal using a patient carb ratio; and adding a correction insulin bolus to the meal bolus in order to take into account the patient's current glucose concentration.

Method 18. The method of any one of Methods 9 to 17, wherein a bolus time variability module calculates a variability in the pre-meal bolus administration time, whereby an occurrence of early/delayed bolus administration is simulated.

Method 19. The method of any one of Methods 9 to 18, wherein an occurrence of missed boluses is simulated by a missed bolus block.

Method 20. The method of any one of Methods 9 to 19, wherein the insulin dose is calculated by adding to a basal insulin rate insulin bolus, and wherein the insulin dose is corrected, using a correction for exercise module, by using information about physical exercise.

Method 21. A method for providing a real-time therapeutic recommendation for use in type 1 diabetes management in a patient, comprising: inputting, to a decision support module, data including continuous glucose monitoring data obtained from a glucose sensor, insulin pump data, and other diabetes management data; generating, based on the input data, a first therapeutic recommendation; displaying the therapeutic recommendation to a patient; inputting, to the decision support model, data indicative of an action taken by the patient in response to receiving the displayed therapeutic recommendation, the data including continuous glucose monitoring data obtained from the glucose sensor and insulin pump data; and generating, based on the input data and the data indicative of an action taken by the patient, a second therapeutic recommendation.

Method 22. The method of Method 21, wherein the continuous glucose monitoring data is selected from the group consisting of a glucose concentration trend, a predicted glucose concentration, a number of past hyperglycemic events, and a number of past hypoglycemic events.

Method 23. The method of any one of Methods 21 to 22, wherein the other diabetes management data is selected from the group consisting of meal data and physical exercise data.

Method 24. The method of any one of Methods 21 to 23, wherein the first therapeutic recommendation or the second therapeutic recommendation is selected from the group consisting of a recommended insulin dose and a basal insulin change.

Method 25. The method of any one of Methods 21 to 24, wherein the first or second therapeutic recommendation is delivered through a smartphone notification.

Method 26. The method of any one of Methods 21 to 25, wherein the decision support module compares the data indicative of an action taken by the patient responsive to the first therapeutic recommendation to determine if the patient has taken the therapeutic recommendation, has ignored the therapeutic recommendation, or has taken an action similar to the therapeutic recommendation.

Method 27. The method of any one of Methods 21 to 26, wherein the action taken by the patient is employed to modify a decision-making module configured to simulate real-life situations and everyday patient behaviors, wherein the decision-making module utilizes self-monitored blood glucose data measurement errors, continuous glucose monitoring data measurement errors, miscalculations of meal carbohydrate content, early insulin administration errors, delayed insulin administration errors, and missed insulin bolus errors.

Method 28. The method of any one of Methods 21 to 27, wherein the decision-making module utilizes patient data to assess glycemic control or efficacy of the decision support module, or to suggest modifications to the decision support module to improve its performance.

Method 29. A method for delivering a therapeutic recommendation for insulin delivery, comprising: collecting data from a patient over a period of time, the data including continuous glucose monitoring data obtained from a glucose sensor and insulin pump data; generating, based on the collected data, a model comprising estimated parameters of the patient's physiology that reproduces the patient's glucose-insulin dynamics; inputting the estimated parameters into a type 1 diabetes patient glucose-insulin model, whereby an individualized patient model is obtained; utilizing the individualized patient model in patient-specific simulations to estimate optimal insulin therapy parameters or individualized guidelines for continuous glucose monitoring-driven insulin dosing; and outputting the optimal insulin therapy parameters.

Method 30. The method of Method 29, wherein outputting the optimal insulin therapy parameters comprises displaying the therapeutic recommendation to a patient on a display.

Method 31. The method of any one of Methods 29 to 30, wherein the display is a smartphone display.

Method 32. The method of any one of Methods 29 to 31, wherein outputting the optimal insulin therapy parameters comprises issuing instructions to an insulin pump for delivering an insulin dose.

Method 33. The method of any one of Methods 29 to 32, wherein utilizing the individualized patient model in patient-specific simulations comprises iteratively running simulations, wherein at the first iteration, the patient's current insulin therapy is implemented, then, at each subsequent iteration, the therapy parameters are updated until it is determined that the therapy parameters satisfy predetermined criteria.

Method 34. The method of any one of Methods 29 to 33, wherein it is determined if the therapy parameters need to be updated by assessing a level of glycemic control.

Any combination of one or more computer readable medium(s) may be utilized in the methods, systems, aspects, and/or embodiments herein. The computer readable medium may be a computer readable signal medium or a computer readable storage medium. A computer readable storage medium may be, for example, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Program code embodied on a computer readable medium may be transmitted using any appropriate medium, including but not limited to wireless, wireline, optical fiber cable, RF, etc., or any suitable combination of the foregoing.

Computer program code for may be written in any combination of one or more programming languages, including an object oriented programming language such as Java, Smalltalk, C++, or the like, and conventional procedural programming languages, such as the "C" programming language or similar programming languages. The program code may execute entirely on the computing unit.

It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

While this specification contains many specific implementation details, these should not be construed as limitations on the claims. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein. It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for providing a real-time therapeutic recommendation for use in type 1 diabetes management in a patient, comprising:
    inputting, to a decision support module, data including continuous glucose monitoring data obtained from a glucose sensor, insulin pump data, and other diabetes management data;
    generating, based on the input data, a first therapeutic recommendation;
    displaying the first therapeutic recommendation to the patient;
    inputting, to the decision support module, data indicative of an action taken by the patient in response to receiving the displayed first therapeutic recommendation, the data including continuous glucose monitoring data obtained from the glucose sensor and insulin pump data;
    comparing the data indicative of an action taken by the patient responsive to the first therapeutic recommendation to determine if the patient has taken the first therapeutic recommendation, has ignored the first therapeutic recommendation, or has taken an action similar to the first therapeutic recommendation; and
    generating, based on the input data and the data indicative of an action taken by the patient, a second therapeutic recommendation, wherein the action taken by the patient is employed to modify a decision-making module configured to simulate real-life situations and behaviors of the patient, and wherein the decision-making module utilizes data of the patient to assess glycemic control or efficacy of the decision support module and to suggest modifications to improve performance of the decision support module.

2. The method of claim 1, wherein the continuous glucose monitoring data is selected from the group consisting of a glucose concentration trend, a predicted glucose concentration, a number of past hyperglycemic events, and a number of past hypoglycemic events.

3. The method of claim 1, wherein the other diabetes management data is selected from the group consisting of meal data and physical exercise data.

4. The method of claim 1, wherein the first therapeutic recommendation or the second therapeutic recommendation is selected from the group consisting of a recommended insulin dose and a basal insulin change.

5. The method of claim 1, wherein the first or second therapeutic recommendation is delivered through a smartphone notification.

6. The method of claim 1, wherein the decision-making module utilizes self-monitored blood glucose data measurement errors, continuous glucose monitoring data measurement errors, miscalculations of meal carbohydrate content, early insulin administration errors, delayed insulin administration errors, and missed insulin bolus errors.

7. The method of claim 1, wherein the other diabetes management data includes meal data.

8. The method of claim 1, wherein the other diabetes management data includes physical exercise data.

9. The method of claim 1, wherein the continuous glucose monitoring data includes a glucose concentration trend.

10. The method of claim 1, wherein the continuous glucose monitoring data includes a predicted glucose concentration.

11. The method of claim 1, wherein the continuous glucose monitoring data includes a number of past hyperglycemic events.

12. The method of claim 1, wherein the continuous glucose monitoring data includes a number of past hypoglycemic events.

13. The method of claim 1, further comprising determining that the action comprises the patient taking the therapeutic recommendation.

14. The method of claim 1, further comprising determining that the action comprises the patient ignoring the therapeutic recommendation.

15. The method of claim 1, further comprising determining that the action comprises the patient taking an action similar to the therapeutic recommendation.

16. The method of claim 1, wherein the first therapeutic recommendation or the second therapeutic recommendation comprises a recommended insulin dose.

17. The method of claim 1, wherein the first therapeutic recommendation or the second therapeutic recommendation comprises a basal insulin change.

18. A method comprising:
    inputting, to a decision support module, data of a patient including continuous glucose monitoring data obtained from a glucose sensor, insulin pump data, and other diabetes management data;
    generating, based on the input data, a first therapeutic recommendation;
    determining, by the decision support module, an action taken by the patient responsive to the first therapeutic recommendation, the action comprising taking the therapeutic recommendation, ignoring the therapeutic recommendation, or taking an action similar to the first therapeutic recommendation; and
    generating, based at least in part on the action taken by the patient, a second therapeutic recommendation, wherein the action taken by the patient is employed to modify a decision-making module configured to simulate real-life situations and behaviors of the patient, and wherein the decision-making module utilizes data of the patient to assess glycemic control or efficacy of the decision support module.

19. The method of claim 18, wherein the decision-making module utilizes self-monitored blood glucose data measurement errors, continuous glucose monitoring data measurement errors, miscalculations of meal carbohydrate content, early insulin administration errors, delayed insulin administration errors, and missed insulin bolus errors.

20. The method of claim 18, wherein the decision-making module utilizes data of the patient to suggest modifications to improve performance of the decision support module.

* * * * *